(12) United States Patent
Dunning

(10) Patent No.: US 8,523,853 B2
(45) Date of Patent: Sep. 3, 2013

(54) HYBRID CONTACT QUALITY MONITORING RETURN ELECTRODE

(75) Inventor: James E. Dunning, Lafayette, CO (US)

(73) Assignee: Covidien LP, Mansfield, MA (US)

( * ) Notice: Subject to any disclaimer, the term of this patent is extended or adjusted under 35 U.S.C. 154(b) by 1102 days.

(21) Appl. No.: 12/358,406

(22) Filed: Jan. 23, 2009

(65) Prior Publication Data

US 2009/0198229 A1 Aug. 6, 2009

Related U.S. Application Data

(60) Provisional application No. 61/026,385, filed on Feb. 5, 2008.

(51) Int. Cl.
*A61B 18/04* (2006.01)
*A61B 18/18* (2006.01)

(52) U.S. Cl.
USPC .................................. 606/33; 606/34; 606/41

(58) Field of Classification Search
USPC ......................................... 606/33–38, 41–42
See application file for complete search history.

(56) References Cited

U.S. PATENT DOCUMENTS

| | | | |
|---|---|---|---|
| 3,913,583 A | 10/1975 | Bross | |
| 3,923,063 A | 12/1975 | Andrews et al. | |
| 4,126,137 A | 11/1978 | Archibald | |
| 4,166,465 A | 9/1979 | Esty et al. | |
| 4,188,927 A | 2/1980 | Harris | |
| 4,200,104 A | 4/1980 | Harris | |
| 4,303,073 A | 12/1981 | Archibald | |
| 4,304,235 A | 12/1981 | Kaufman | |
| 4,387,714 A | 6/1983 | Geddes et al. | |
| 4,494,541 A | 1/1985 | Archibald | |
| 4,669,468 A | 6/1987 | Cartmell et al. | |
| 4,788,977 A | 12/1988 | Farin et al. | |
| 4,799,480 A | 1/1989 | Abraham et al. | |
| 4,844,063 A | 7/1989 | Clark | |
| 4,942,313 A | 7/1990 | Kinzel | |
| 5,042,981 A | 8/1991 | Gross | |
| 5,087,257 A | 2/1992 | Farin et al. | |
| 5,246,439 A | 9/1993 | Hebborn et al. | |
| 5,312,401 A | 5/1994 | Newton et al. | |
| 5,370,645 A | 12/1994 | Klicek et al. | |
| 5,452,725 A | 9/1995 | Martenson | |
| 5,678,545 A | 10/1997 | Stratbucker | |

(Continued)

FOREIGN PATENT DOCUMENTS

| | | |
|---|---|---|
| CA | 1219642 | 3/1987 |
| DE | 3206947 | 9/1983 |

(Continued)

OTHER PUBLICATIONS

U.S. Appl. No. 10/696,946, filed Jun. 30, 2003.

(Continued)

*Primary Examiner* — Nicholas Lucchesi
*Assistant Examiner* — Rebecca E Eisenberg

(57) ABSTRACT

An electrosurgical return electrode is disclosed. The return electrode includes an intermediary layer formed from a dielectric material, the intermediary layer having a top surface and a patient-contacting surface. The return electrode also includes a capacitive return electrode formed from a conductive material disposed on the top surface of the intermediary layer and a resistive monitoring electrode formed from a conductive material disposed on the patient-contact surface of the intermediary layer.

10 Claims, 4 Drawing Sheets

(56) References Cited

U.S. PATENT DOCUMENTS

| | | | |
|---|---|---|---|
| 5,688,269 | A | 11/1997 | Newton et al. |
| 5,695,494 | A | 12/1997 | Becker |
| 5,720,744 | A | 2/1998 | Eggleston et al. |
| 5,830,212 | A | 11/1998 | Cartmell et al. |
| 5,836,942 | A | 11/1998 | Netherly et al. |
| 5,868,742 | A | 2/1999 | Manes et al. |
| 5,947,961 | A | 9/1999 | Netherly |
| 5,971,981 | A | 10/1999 | Hill et al. |
| 6,007,532 | A | 12/1999 | Netherly |
| 6,053,910 | A | 4/2000 | Fleenor |
| 6,083,221 | A | 7/2000 | Fleenor et al. |
| 6,171,304 | B1 | 1/2001 | Netherly et al. |
| 6,214,000 | B1 | 4/2001 | Fleenor et al. |
| 6,310,611 | B1 | 10/2001 | Caldwell |
| 6,413,255 | B1 | 7/2002 | Stern |
| 6,454,764 | B1 | 9/2002 | Fleenor et al. |
| 6,544,258 | B2 | 4/2003 | Fleenor et al. |
| 6,582,424 | B2 | 6/2003 | Fleenor et al. |
| 6,666,859 | B1 | 12/2003 | Fleenor et al. |
| 6,860,881 | B2 | 3/2005 | Sturm et al. |
| 7,160,293 | B2 | 1/2007 | Sturm et al. |
| 7,166,102 | B2 | 1/2007 | Fleenor et al. |
| 7,169,145 | B2 | 1/2007 | Isaacson et al. |
| 7,267,675 | B2 | 9/2007 | Stern et al. |
| 7,422,589 | B2 | 9/2008 | Newton et al. |
| 2003/0139741 | A1 | 7/2003 | Goble et al. |
| 2005/0085806 | A1 | 4/2005 | Auge et al. |
| 2006/0041251 | A1 | 2/2006 | Odell et al. |
| 2006/0041252 | A1 | 2/2006 | Odell et al. |
| 2006/0074411 | A1 | 4/2006 | Carmel et al. |
| 2007/0049916 | A1 | 3/2007 | Isaacson et al. |
| 2007/0073284 | A1 | 3/2007 | Sturm et al. |
| 2007/0167942 | A1 | 7/2007 | Rick |
| 2007/0244478 | A1* | 10/2007 | Bahney ............ 606/32 |
| 2008/0281309 | A1 | 11/2008 | Dunning et al. |
| 2008/0281310 | A1 | 11/2008 | Dunning et al. |
| 2008/0281311 | A1 | 11/2008 | Dunning et al. |

FOREIGN PATENT DOCUMENTS

| | | |
|---|---|---|
| DE | 3544443 | 6/1987 |
| DE | 4238263 | 5/1993 |
| DE | 4231236 | 3/1994 |
| DE | 19717411 | 11/1998 |
| DE | 19801173 | 7/1999 |
| DE | 10328514 | 6/2003 |
| DE | 102004010940 | 9/2005 |
| EP | 0262888 | 4/1988 |
| EP | 390937 | 10/1990 |
| EP | 836868 | 4/1998 |
| EP | 0930048 | 7/1999 |
| EP | 1051949 | 11/2000 |
| EP | 1076350 | 2/2001 |
| EP | 1468653 | 10/2004 |
| EP | 1645236 | 4/2006 |
| EP | 1707151 | 10/2006 |
| EP | 1808144 | 7/2007 |
| EP | 1902684 | 3/2008 |
| FR | 2276027 | 6/1974 |
| FR | 2516782 | 5/1983 |
| GB | 2054382 | 2/1981 |
| GB | 2374532 | 10/2002 |
| WO | WO 97/37719 | 10/1997 |
| WO | WO 98/18395 | 5/1998 |
| WO | WO 99/09899 | 3/1999 |
| WO | WO 99/11187 | 3/1999 |
| WO | WO 00/32122 | 6/2000 |
| WO | WO 00/53113 | 9/2000 |
| WO | WO 00/65993 | 11/2000 |
| WO | WO 01/87175 | 11/2001 |
| WO | WO 02/058579 | 8/2002 |
| WO | WO 02/060526 | 8/2002 |
| WO | WO 03/094766 | 11/2003 |
| WO | WO 2004/028385 | 4/2004 |
| WO | WO 2005/087124 | 9/2005 |
| WO | WO 2005/099606 | 10/2005 |
| WO | WO 2005/115262 | 12/2005 |
| WO | WO 2008/009385 | 1/2008 |

OTHER PUBLICATIONS

U.S. Appl. No. 11/900,190, filed Sep. 10, 2007.
U.S. Appl. No. 12/396,814, filed Mar. 3, 2009.
U.S. Appl. No. 12/395,812, filed Mar. 2, 2009.
U.S. Appl. No. 12/364,624, filed Feb. 3, 2009.
U.S. Appl. No. 12/335,281, filed Jan. 16, 2009.
U.S. Appl. No. 12/401,428, filed Mar. 10, 2009.
U.S. Appl. No. 12/407,008, filed Mar. 19, 2009.
Boyles, Walt; "Instrumentation Reference Book", 2002; Butterworth-Heinemann ; 262-264.
International Search Report EP05002027.0 dated May 12, 2005.
International Search Report EP05021944.3 dated Jan. 25, 2006.
International Search Report EP06006961 dated Aug. 3, 2006.
International Search Report EP06006961.4 dated Oct. 5, 2007.
International Search Report EP06018206.0 dated Oct. 13, 2006.
International Search Report EP06023756.7 dated Feb. 21, 2008.
International Search Report EP07000567.3 dated Dec. 3, 2008,.
International Search Report EP07000885.9 dated May 15, 2007.
International Search Report EP07007783.9 dated Aug. 6, 2007.
International Search Report EP07018375.1 dated Jan. 8, 2008.
International Search Report EP07019173.9 dated Feb. 12, 2008.
International Search Report EP07019178.8 dated Feb. 12, 2008.
International Search Report EP07253835.8 dated Feb. 20, 2007.
International Search Report EP08006731.7 dated Jul. 29, 2008.
International Search Report EP08006734.1 dated Aug. 18, 2008.
International Search Report EP08006735.8 dated Jan. 8, 2009.
International Search Report EP08008510.3 dated Oct. 27, 2008.
International Search Report EP08013758.1 dated Nov. 20, 2008.
International Search Report EP08013760.7 dated Nov. 20, 2008.
International Search Report EP08155779-partial dated Sep. 8, 2008.
International Search Report EP08155779 dated Jan. 23, 2009.
International Search Report EP09152032 dated Jun. 17, 2009.
International Search Report EP09152130.2 dated Apr. 6,2009.
International Search Report PCT/US2004/004196 dated Oct. 4, 2007.

* cited by examiner

HYBRID CONTACT QUALITY MONITORING RETURN ELECTRODE

CROSS-REFERENCE TO RELATED APPLICATIONS

This application claims the benefit of priority to U.S. Provisional Application Ser. No. 61/026,385 entitled "HYBRID CONTACT QUALITY MONITORING RETURN ELECTRODE" filed Feb. 5, 2008 by James E. Dunning, which is incorporated by reference herein.

BACKGROUND

1. Technical Field

The present disclosure relates to electrosurgical apparatuses, systems and methods. More particularly, the present disclosure is directed to electrosurgical systems utilizing one or more capacitive return electrodes configured to monitor contact quality thereof.

2. Background of Related Art

Energy-based tissue treatment is well known in the art. Various types of energy (e.g., electrical, ultrasonic, microwave, cryogenic, heat, laser, etc.) are applied to tissue to achieve a desired result. Electrosurgery involves application of high radio frequency electrical current to a surgical site to cut, ablate, coagulate or seal tissue. In monopolar electrosurgery, the active electrode is typically part of the surgical instrument held by the surgeon and applied to the tissue to be treated. A patient return electrode is placed remotely from the active electrode to carry the current back to the generator and safely disperse current applied by the active electrode.

The return electrodes usually have a large patient contact surface area to minimize heating at that site. Heating is caused by high current densities which directly depend on the surface area. A larger surface contact area results in lower localized heat intensity. Return electrodes are typically sized based on assumptions of the maximum current utilized during a particular surgical procedure and the duty cycle (i.e., the percentage of time the generator is on).

The first types of return electrodes were in the form of large metal plates covered with conductive jelly. Later, adhesive electrodes were developed with a single metal foil covered with conductive jelly or conductive adhesive. However, one problem with these adhesive electrodes was that if a portion peeled from the patient, the contact area of the electrode with the patient decreased, thereby increasing the current density at the adhered portion and, in turn, increasing the heating at the tissue. This risked burning the patient in the area under the adhered portion of the return electrode if the tissue was heated beyond the point where circulation of blood could cool the skin.

To address this problem various return electrodes and hardware circuits, generically called Return Electrode Contact Quality Monitors (RECQMs), were developed. Such systems relied on measuring impedance at the return electrode to calculate a variety of tissue and/or electrode properties. These systems were configured to measure changes in impedance of the return electrodes to detect peeling. Furthermore, the systems were designed to work with conventional resistive return electrodes.

SUMMARY

The present disclosure relates to electrosurgical return electrodes. Disclosure provides for a hybrid return electrode having a capacitive return electrode and a resistive monitoring electrode which includes one or more pairs of split conductors. The dual nature of the hybrid return electrodes provides for increased heat dispersion as well as return electrode monitoring.

According to one aspect of the present disclosure an electrosurgical return electrode is disclosed. The return electrode includes an intermediary layer formed from a dielectric material, the intermediary layer having a top surface and a patient-contacting surface. The return electrode also includes a capacitive return electrode formed from a conductive material disposed on the top surface of the intermediary layer and a resistive monitoring electrode formed from a conductive material disposed on the patient-contact surface of the intermediary layer.

According to another aspect of the present disclosure an electrosurgical system is provided. The system includes one or more electrosurgical return electrodes, each of which includes an intermediary layer formed from a dielectric material, the intermediary layer having a top surface and a patient-contacting surface. The return electrode also includes a capacitive return electrode formed from a conductive material disposed on the top surface of the intermediary layer and a resistive monitoring electrode formed from a conductive material disposed on the patient-contact surface of the intermediary layer. The resistive monitoring electrode includes one or more pairs of split electrode conductors. The system also includes a return electrode monitoring system coupled to one or more pairs of split electrode conductors and configured to measure impedance between the one or more pairs of split electrode conductors.

A method for manufacturing an electrosurgical return electrode is also contemplated by the present disclosure. The method includes the steps of forming an intermediary layer from a dielectric material, the intermediary layer having a top surface and a patient-contacting surface. The method also includes the steps of depositing a first conductive material onto the top surface of the intermediary layer to form a capacitive return electrode and depositing a second conductive material onto the patient-contact surface of the intermediary layer to form a resistive monitoring electrode. The method further includes the step of heating the intermediary layer, capacitive return electrode and resistive monitoring electrode for a predetermined period of time at a temperature from about 70° C. to about 120° C.

BRIEF DESCRIPTION OF THE DRAWINGS

Various embodiments of the present disclosure are described herein with reference to the drawings wherein.

DETAILED DESCRIPTION

Particular embodiments of the present disclosure are described hereinbelow with reference to the accompanying drawings. In the following description, well-known functions or constructions are not described in detail to avoid obscuring the present disclosure in unnecessary detail.

A capacitive return electrode can safely return more current than a return electrode incorporating a resistive design. However, conventional capacitive return electrodes are not configured to couple with a return electrode monitoring ("REM") system. The REM system monitors the adherence of the return electrode to the patient by measuring the impedance and/or current between one or more split conductors. Split conductor designs are incorporated into resistive return electrodes but previously are not included in capacitive return electrode designs due to the increased impedance of these return electrodes.

The present disclosure provides for a hybrid return electrode incorporating capacitive and return electrode monitoring technologies. More specifically, the hybrid return electrode according to the present disclosure includes a dielectric layer and a solid metal layer (e.g., silver) deposited on a top (e.g., outside) surface providing for a capacitive configuration. The hybrid return electrode also includes one or more pairs of split metallic conductors (e.g., silver foil) disposed on a bottom (e.g., patient contact) surface of the dielectric layer. The split metallic conductors serve as a resistive monitoring electrode which is interrogated by the REM system to determine contact quality of the hybrid return electrode.

Figure 1:
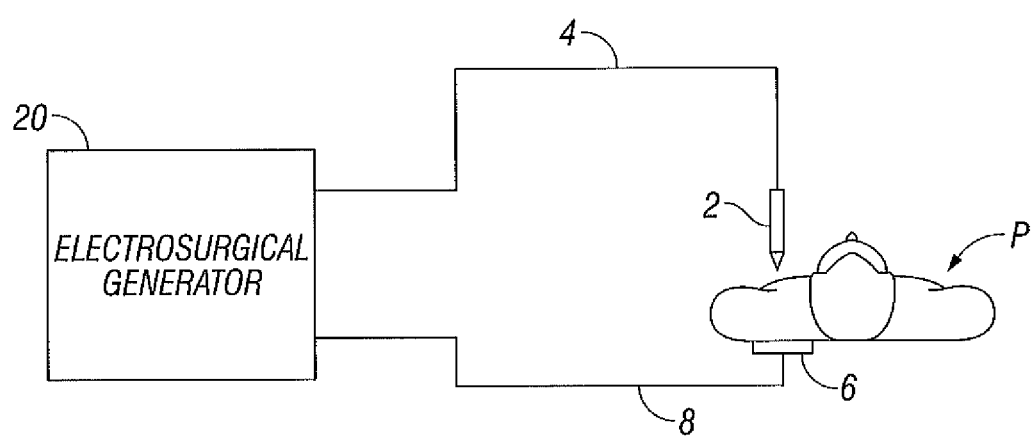
FIG. 1 is a schematic block diagram of an electrosurgical system according to the present disclosure.

FIG. 1 is a schematic illustration of an electrosurgical system according to one embodiment of the present disclosure. The system includes an electrosurgical instrument 2 having one or more electrodes for treating tissue of a patient P. The instrument 2 is a monopolar instrument including one or more active electrodes (e.g., electrosurgical cutting probe, ablation electrode(s), etc.). Electrosurgical RF energy is supplied to the instrument 2 by a generator 20 via an electrosurgical cable 4, which is connected to an active output terminal, allowing the instrument 2 to coagulate, ablate and/or otherwise treat tissue. The energy is returned to the generator 20 through a hybrid return electrode 6 via a return cable 8. The system may include a plurality of return electrodes 6 that are arranged to minimize the chances of tissue damage by maximizing the overall contact area with the patient P. In addition, the generator 20 and the return electrode 6 may be configured for monitoring so-called "tissue-to-patient" contact to insure that sufficient contact exists therebetween to further minimize chances of tissue damage.

The generator 20 includes input controls (e.g., buttons, activators, switches, touch screen, etc.) for controlling the generator 20. In addition, the generator 20 may include one or more display screens for providing the user with variety of output information (e.g., intensity settings, treatment complete indicators, etc.). The controls allow the user to adjust power of the RF energy, waveform, and other parameters to achieve the desired waveform suitable for a particular task (e.g., coagulating, tissue sealing, intensity setting, etc.). The instrument 2 may also include a plurality of input controls that may be redundant with certain input controls of the generator 20. Placing the input controls at the instrument 2 allows for easier and faster modification of RF energy parameters during the surgical procedure without requiring interaction with the generator 20.

Figure 2:
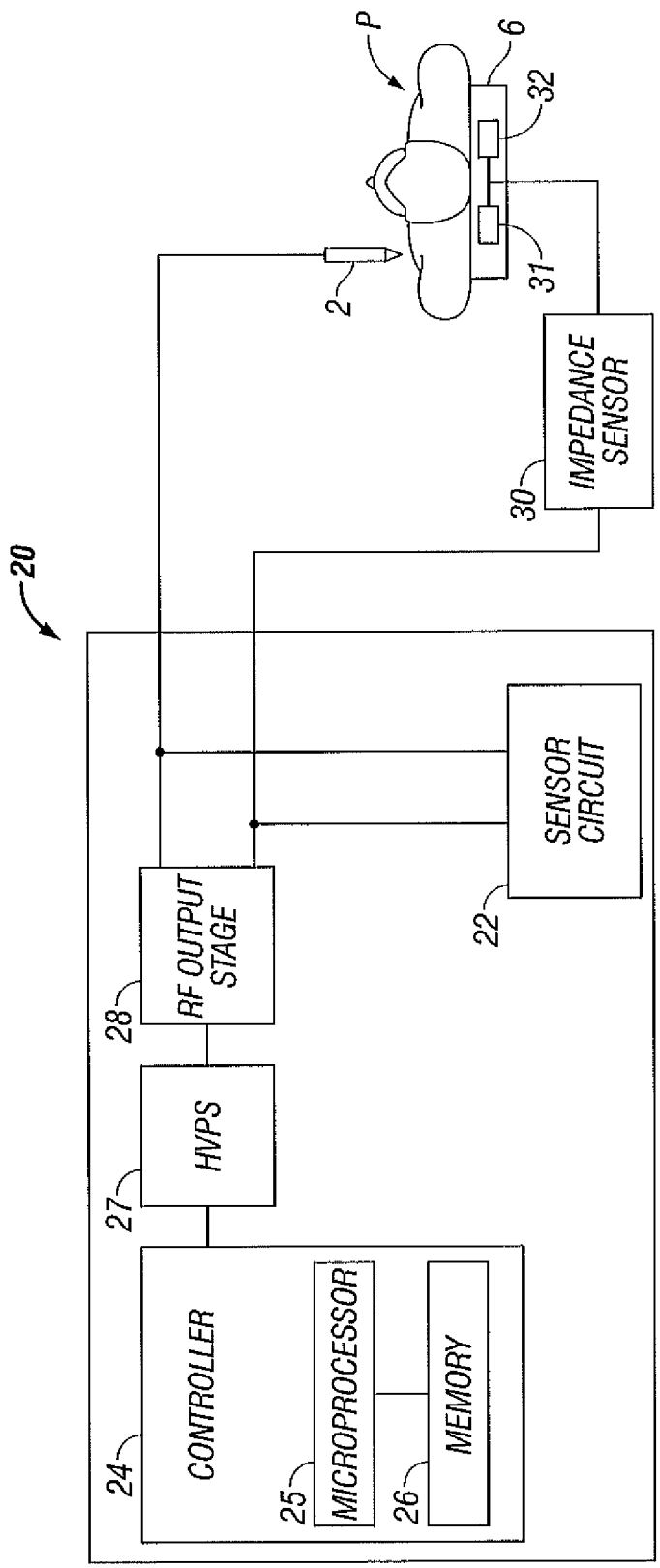
FIG. 2 is a schematic block diagram of a generator according to one embodiment of the present disclosure.

FIG. 2 shows a schematic block diagram of the generator 20 having a controller 24, a high voltage DC power supply 27 ("HVPS") and an RF output stage 28. The HVPS 27 provides high voltage DC power to an RF output stage 28, which then converts high voltage DC power into RF energy and delivers the RF energy to the active electrode. In particular, the RF output stage 28 generates sinusoidal waveforms of high RF energy. The RF output stage 28 is configured to generate a plurality of waveforms having various duty cycles, peak voltages, crest factors, and other suitable parameters. Certain types of waveforms are suitable for specific electrosurgical modes. For instance, the RF output stage 28 generates a 100% duty cycle sinusoidal waveform in cut mode, which is best suited for ablating, fusing and dissecting tissue, and a 1-25% duty cycle waveform in coagulation mode, which is best used for cauterizing tissue to stop bleeding.

The controller 24 includes a microprocessor 25 operably connected to a memory 26, which may be volatile type memory (e.g., RAM) and/or non-volatile type memory (e.g., flash media, disk media, etc.). The microprocessor 25 includes an output port that is operably connected to the HVPS 27 and/or RF output stage 28 that allows the microprocessor 25 to control the output of the generator 20 according to either open and/or closed control loop schemes. Those skilled in the art will appreciate that the microprocessor 25 may be substituted by any logic processor (e.g., control circuit) adapted to perform the calculations discussed herein.

A closed loop control scheme is a feedback control loop wherein sensor circuit 22, which may include a plurality of sensors measuring a variety of tissue and energy properties (e.g., tissue impedance, tissue temperature, output current and/or voltage, etc.), provides feedback to the controller 24. Such sensors are within the purview of those skilled in the art. The controller 24 then signals the HVPS 27 and/or RF output stage 28, which then adjust DC and/or RF power supply, respectively. The controller 24 also receives input signals from the input controls of the generator 20 or the instrument 2. The controller 24 utilizes the input signals to adjust power outputted by the generator 20 and/or performs other control functions thereon.

The generator 20 includes a return electrode monitoring system having an impedance monitor 30 which is coupled to a pair of split electrode conductors 31 and 32 disposed within the return electrode 6. The impedance sensor 30 measures the impedance between the split electrode conductors 31 and 32 and transmits the measurements to the sensor circuit 22 which analyzes the impedance measurement to determine an adherence factor (e.g., the degree of adherence) of the return electrode 6 to the patient. If impedance between the split electrode conductors 31 and 32 decreases, the sensor circuit 22 recognizes that the return electrode 6 is peeling and notifies the user of the event via an alarm and/or terminates the supply of RF energy.

Figure 3:
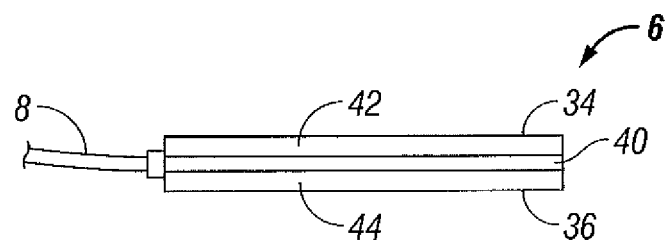
FIG. 3 is a cross-sectional side view of an electrosurgical return electrode of the electrosurgical system of FIG. 1.
Figure 4:
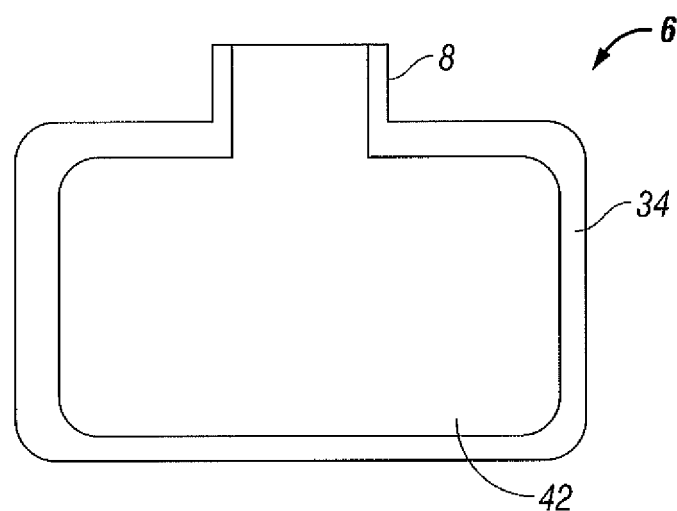
FIG. 4 is a top view of the intermediary layer of the electrosurgical return electrode of FIG. 3.
Figure 5:
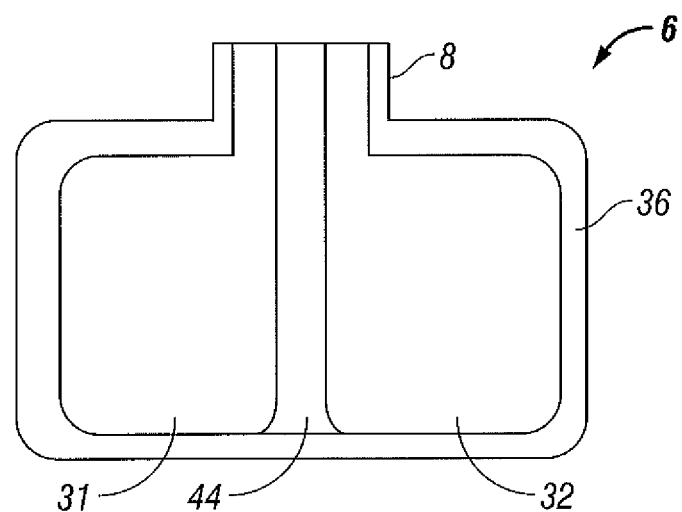
FIG. 5 is a bottom view the intermediary layer of the electrosurgical return electrode of FIG. 3.

FIGS. 3-5 illustrate the hybrid return electrode 6 having a top surface 34 and a patient-contacting surface 36. While the return electrode 6 is depicted as having a general rectangular shape, it is within the scope of the disclosure for the return electrode 6 to have any suitable regular or irregular shape. The return electrode 6 may include an adhesive material layer on the patient-contacting surface 36. The adhesive material can be, but is not limited to, a polyhesive adhesive, a Z-axis adhesive, a water-insoluble, hydrophilic, pressure-sensitive adhesive, or any combinations thereof, such as POLYHESIVE™ adhesive manufactured by Valleylab, a division of Covidien of Boulder, Colo. The adhesive may be conductive or dielectric. The adhesive material layer ensures an optimal surface contact area between the electrosurgical return electrode 6 and the patient "P," which limits the possibility of a patient burn.

The return electrode 6 includes an intermediary dielectric layer 40 which can be formed from a variety of flexible polymer materials such as polyimide film sold under a trademark KAPTON™ and polyester film, such as biaxially-oriented polyethylene terephthalate (boPET) polyester film sold under trademarks MYLAR™ and MELINEX™.

The return electrode 6 also includes a capacitive return electrode 42 disposed on the top surface of the intermediary dielectric layer 40. The capacitive return electrode 42 may be formed from a suitable conductive material (e.g., metal) adapted to conduct the electrosurgical energy from the surgical site to the generator 20. In embodiments, a variety of conductive metals may be used, such as silver, copper, gold, stainless steel, various alloys formed therefrom and the like. The capacitive return electrode 42 may be deposited directly as a solid contiguous metallic layer onto the dielectric layer 40 by using a variety of methods such as screen printing, spraying, painting and the like. The shape of the capacitive return electrode 42 may conform to the shape of the dielectric layer 40, such that the edges of the capacitive return electrode 42 do not overhang the dielectric layer 40 to prevent direct contact between the capacitive return electrode 42 and the patient. Since the capacitive return electrode 42 is separated from the patient P via the dielectric layer 40, the combination of the dielectric layer 40 and the capacitive return layers 42 act as a capacitor. This provides for more even heating throughout the return electrode 6 eliminating creation of so-called "hot spots" which can lead to tissue damage.

The return electrode 6 also includes a resistive monitoring electrode 44 disposed on the patient-contacting surface of the dielectric layer 40. The resistive monitoring electrode 44 may also be formed from a suitable conductive material (e.g., metal) such as silver, copper, gold, stainless steel, etc. and may be deposited directly onto the dielectric layer 40 by using similar methods such as screen printing and the like. The monitoring electrode 44 includes a pair of split electrode conductors 31 and 32 which are separated from one another and are coupled to the impedance sensor 30. The addition of the monitoring electrode 44 having split electrode conductors 31 and 32 allows for return electrode monitoring. The impedance sensor 30 interrogates the split electrode conductors 31 and 32 to determine impedance therein and thereby calculate the adherence factor of the return electrode 6. Return electrode monitoring is technically impracticable utilizing only a simple capacitive return electrode due to the increased impedance thereof. The hybrid return electrode 6 according to the present disclosure combines both, capacitive return electrode 42 and resistive monitoring electrode 44 with the dielectric layer 40 disposed therebetween, allowing for combination of both technologies.

Figure 6:
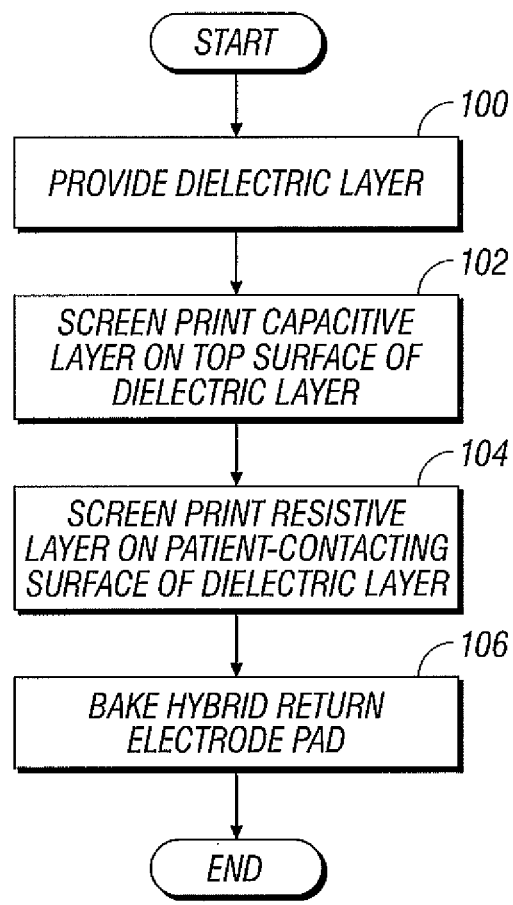
FIG. 6 shows a flow chart diagram illustrating a method for manufacturing the electrosurgical return electrode of FIG. 3.

FIG. 6 illustrates a method for manufacturing the hybrid return electrode 6. In step 100, the dielectric layer 40 is formed by layering a plurality of polymer films. In one embodiment, the layer 40 may be formed using a molding process. The dielectric layer 40 is thereafter shaped to desired dimensions. In step 102, the metal forming the capacitive return electrode 42 is screen printed onto the top surface of the dielectric layer 40. In step 104, the resistive monitoring electrode 44 is also screen printed onto the dielectric layer 40, but onto the patient-contacting side. In embodiments, the metal being used is silver due to high conductivity and resistance to corrosion thereof. In step 106, the combined dielectric layer 40, the capacitive return electrode 42 and resistive monitoring electrode 44 are heat treated at a temperature from about 70° C. to about 120° C. for a predetermined period of time (e.g., 5 minutes to 6 hours). The treatment temperature depends on the material of the dielectric layer 40, such as if polyimide film was used, hotter temperatures can be used and if polyester film was used cooler temperature must be used. Various other materials and deposition methods are envisioned which are suitable for deposition of metals directly onto a dielectric layer.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electrosurgical return electrode, comprising:
   an intermediary layer formed from a dielectric material, the intermediary layer having a top surface and a patient-contacting surface;
   a capacitive return electrode formed from a conductive material disposed on the top surface of the intermediary layer; and
   a resistive monitoring electrode formed from a conductive material disposed on the patient-contact surface of the intermediary layer, wherein the resistive monitoring electrode includes at least one pair of split electrode conductors.

2. An electrosurgical return electrode according to claim 1, wherein the at least one pair of split electrode conductors are adapted to couple to a return electrode monitoring system.

3. An electrosurgical return electrode according to claim 1, wherein the capacitive return electrode and the resistive monitoring electrode are screen printed onto the intermediary layer.

4. An electrosurgical return electrode according to claim 1, wherein the conductive material is selected from the group consisting of silver, copper, gold and stainless steel.

5. An electrosurgical return electrode according to claim 1, wherein the dielectric material is selected from the group consisting of polyimide film and polyester film.

6. An electrosurgical system comprising:
   at least one electrosurgical return electrode, comprising:
      an intermediary layer formed from a dielectric material, the intermediary layer having a top surface and a patient-contacting surface;
      a capacitive return electrode formed from a conductive material disposed on the top surface of the intermediary layer; and
      a resistive monitoring electrode formed from a conductive material disposed on the patient-contact surface of the intermediary layer, wherein the resistive monitoring electrode includes at least one pair of split electrode conductors; and
   a return electrode monitoring system coupled to the at least one pair of split electrode conductors and configured to measure impedance between the at least one pair of split electrode conductors.

7. An electrosurgical system according to claim 6, wherein the return electrode monitoring system is adapted to couple to a sensor circuit that is configured to determine adherence factor of the at least one electrosurgical return electrode as a function of the impedance between one electrode pad of the at least one pair of split electrode conductors.

8. An electrosurgical system according to claim 6, wherein the capacitive return electrode and the resistive monitoring electrode are screen printed onto the intermediary layer.

9. An electrosurgical system according to claim 6, wherein the conductive material is selected from the group consisting of silver, copper, gold and stainless steel.

10. An electrosurgical system according to claim 6, wherein the dielectric material is selected from the group consisting of polyimide film and polyester film.

* * * * *